United States Patent
MacTaggart et al.

(10) Patent No.: US 11,857,443 B2
(45) Date of Patent: **\*Jan. 2, 2024**

(54) AUTOMATED RETRIEVABLE HEMORRHAGE CONTROL SYSTEM

(71) Applicant: Board of Regents of the University of Nebraska, Lincoln, NE (US)

(72) Inventors: Jason N. MacTaggart, Omaha, NE (US); Alexey Kamenskiy, Omaha, NE (US)

(73) Assignee: Board of Regents of the University of Nebraska, Lincoln, NE (US)

(\*) Notice: Subject to any disclaimer, the term of this patent is extended or adjusted under 35 U.S.C. 154(b) by 826 days.

This patent is subject to a terminal disclaimer.

(21) Appl. No.: 16/941,867

(22) Filed: Jul. 29, 2020

(65) Prior Publication Data

US 2020/0352758 A1    Nov. 12, 2020

Related U.S. Application Data

(63) Continuation of application No. 15/556,922, filed as application No. PCT/US2016/021728 on Mar. 10, 2016, now Pat. No. 10,758,386.

(Continued)

(51) Int. Cl.
*A61F 2/958* (2013.01)
*A61F 2/07* (2013.01)
(Continued)

(52) U.S. Cl.
CPC ............... *A61F 2/958* (2013.01); *A61B 5/02* (2013.01); *A61B 5/02042* (2013.01);
(Continued)

(58) Field of Classification Search
CPC ............ A61B 5/6862; A61B 17/12036; A61B 17/12045; A61B 17/12109;
(Continued)

(56) References Cited

U.S. PATENT DOCUMENTS 5,360,403 A    11/1994   Mische
5,728,068 A    3/1998    Leone et al.
(Continued)

FOREIGN PATENT DOCUMENTS

WO    WO 96/38109    12/1996
WO    WO 2000/53240    9/2000
(Continued)

OTHER PUBLICATIONS

PCT International Preliminary Report on Patentability in Application No. PCT/US2016/021728, dated Sep. 21, 2017, 12 pages.
(Continued)

*Primary Examiner* — Timothy J Neal
*Assistant Examiner* — Andrew P. Restaino
(74) *Attorney, Agent, or Firm* — Fish & Richardson P.C.

(57) ABSTRACT

Some implementations of an endovascular device include a stent graft with an expandable tubular metallic frame and a covering material disposed on at least a portion of the metallic frame. The stent graft defines a lumen therethrough. In a particular embodiment, a first balloon is disposed around an outer periphery of the stent graft, a second balloon is disposed around the outer periphery of the stent graft and spaced apart from the first balloon, and a third balloon is disposed within the stent graft lumen between the first balloon and the second balloon. The third balloon can be inflated to fully or partially occlude the lumen. The first and second balloons can be individually inflated to fully or partially shunt blood flow from a blood vessel through the stent graft. In some embodiments, sensors and an automated control unit are included to automate the operations of the endovascular device.

20 Claims, 7 Drawing Sheets

Related U.S. Application Data

(60) Provisional application No. 62/162,966, filed on May 18, 2015, provisional application No. 62/131,574, filed on Mar. 11, 2015.

(51) Int. Cl.

| | | |
|---|---|---|
| *A61B 17/12* | (2006.01) | |
| *A61F 2/95* | (2013.01) | |
| *A61B 5/00* | (2006.01) | |
| *A61B 5/02* | (2006.01) | |
| *A61B 17/00* | (2006.01) | |
| *A61B 5/0215* | (2006.01) | |
| *A61B 5/024* | (2006.01) | |
| *A61B 5/145* | (2006.01) | |
| *A61B 5/0205* | (2006.01) | |
| *A61F 2/06* | (2013.01) | |

(52) U.S. Cl.
CPC ...... *A61B 5/6862* (2013.01); *A61B 17/12036* (2013.01); *A61B 17/12045* (2013.01); *A61B 17/12109* (2013.01); *A61B 17/12118* (2013.01); *A61B 17/12136* (2013.01); *A61F 2/07* (2013.01); *A61B 5/024* (2013.01); *A61B 5/02055* (2013.01); *A61B 5/02158* (2013.01); *A61B 5/14539* (2013.01); *A61B 5/14542* (2013.01); *A61B 5/6853* (2013.01); *A61B 2017/00017* (2013.01); *A61B 2017/00022* (2013.01); *A61F 2/9522* (2020.05); *A61F 2002/061* (2013.01); *A61F 2002/077* (2013.01); *A61F 2002/9528* (2013.01); *A61F 2230/0067* (2013.01); *A61F 2230/0069* (2013.01); *A61F 2250/001* (2013.01); *A61F 2250/0002* (2013.01); *A61F 2250/0003* (2013.01); *A61F 2250/0024* (2013.01); *A61F 2250/0039* (2013.01); *A61F 2250/0059* (2013.01); *A61F 2250/0069* (2013.01); *A61F 2250/0096* (2013.01)

(58) Field of Classification Search
CPC ......... A61B 17/12118; A61B 17/12136; A61F 2230/0067; A61F 2230/0069; A61F 2250/0003; A61F 2250/001; A61F 2250/0039; A61F 2250/0069; A61F 2002/061; A61F 2/07; A61F 2/958
See application file for complete search history.

(56) References Cited

U.S. PATENT DOCUMENTS

| | | |
|---|---|---|
| 6,148,825 A | 11/2000 | Anderson et al. |
| 6,210,318 B1 | 4/2001 | Lederman |
| 6,309,350 B1 | 10/2001 | VanTassel |
| 6,827,735 B2 | 12/2004 | Greensberg |
| 6,840,956 B1 | 1/2005 | Wolinsky et al. |
| 2003/0229388 A1 | 12/2003 | Hayashi et al. |
| 2006/0122522 A1 | 6/2006 | Chavan et al. |
| 2009/0030331 A1 | 1/2009 | Hochareon |
| 2010/0324649 A1 | 12/2010 | Mattsson et al. |
| 2012/0191174 A1 | 7/2012 | Vinluan |
| 2014/0039537 A1 | 2/2014 | Carrison |
| 2014/0336690 A1* | 11/2014 | Zhadkevich ..... A61B 17/12036 606/194 |
| 2018/0064565 A1 | 3/2018 | MacTaggart |

FOREIGN PATENT DOCUMENTS

| | | |
|---|---|---|
| WO | WO 2010/029190 | 3/2010 |
| WO | WO 2016/008521 | 1/2016 |

OTHER PUBLICATIONS

PCT International Search Report and Written Opinion in Application No. PCT/US2016/021728, dated Jun. 3, 2016, 13 pages.
European Extended Search Report in European Application No. 16762492.3, dated Feb. 16, 2018, 8 pages.

\* cited by examiner

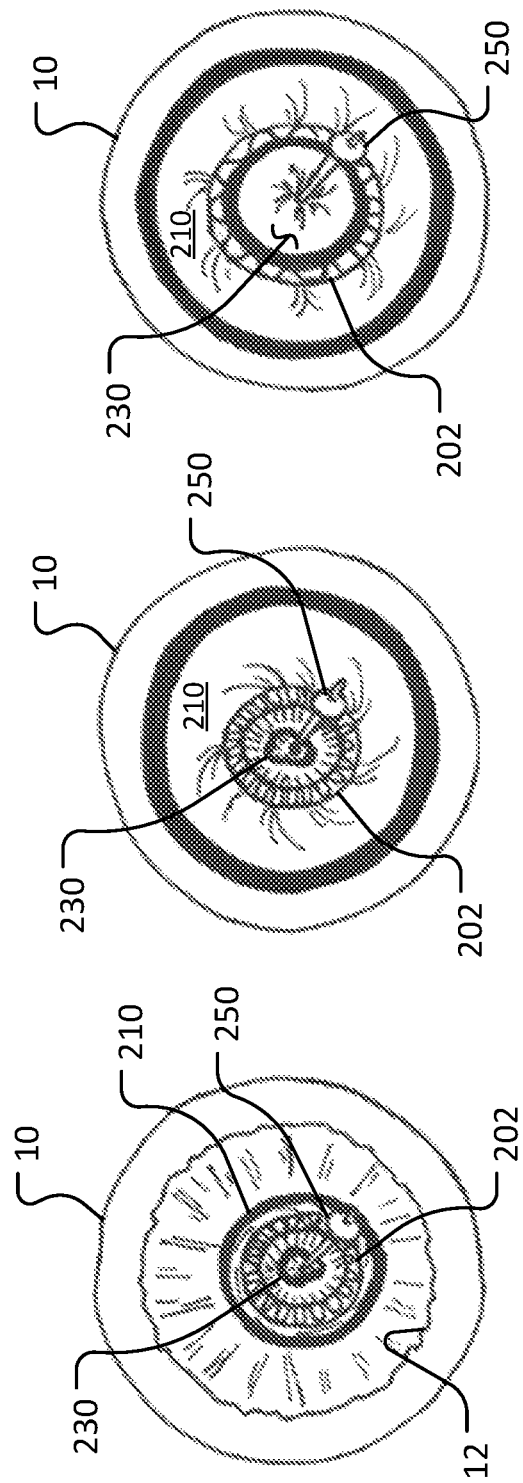

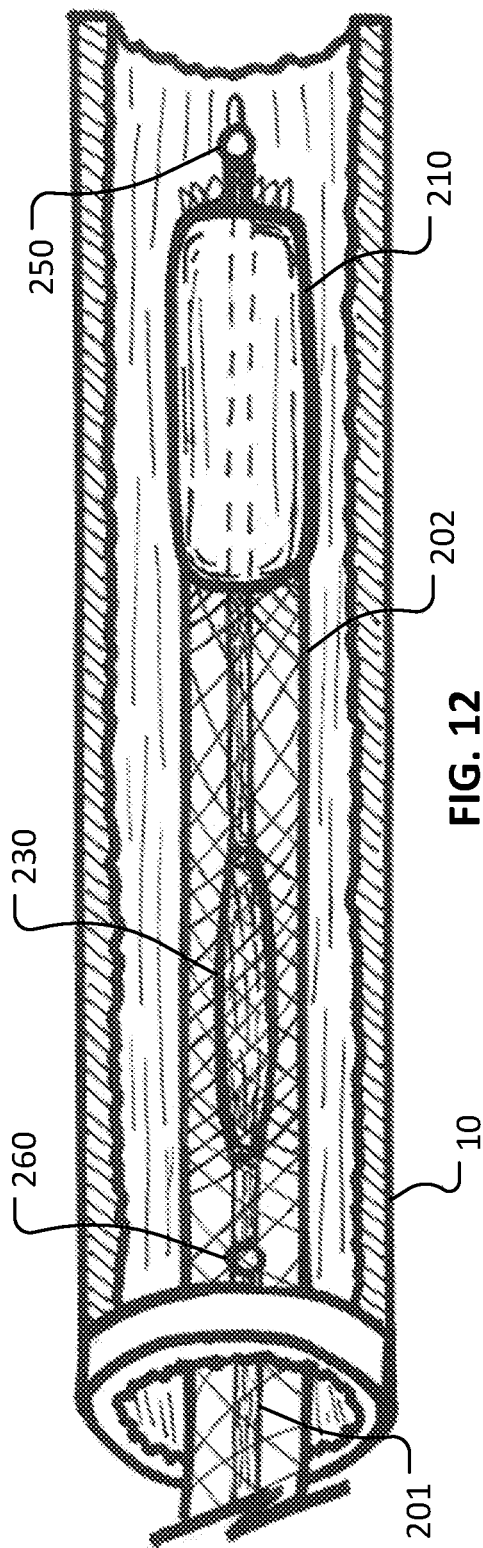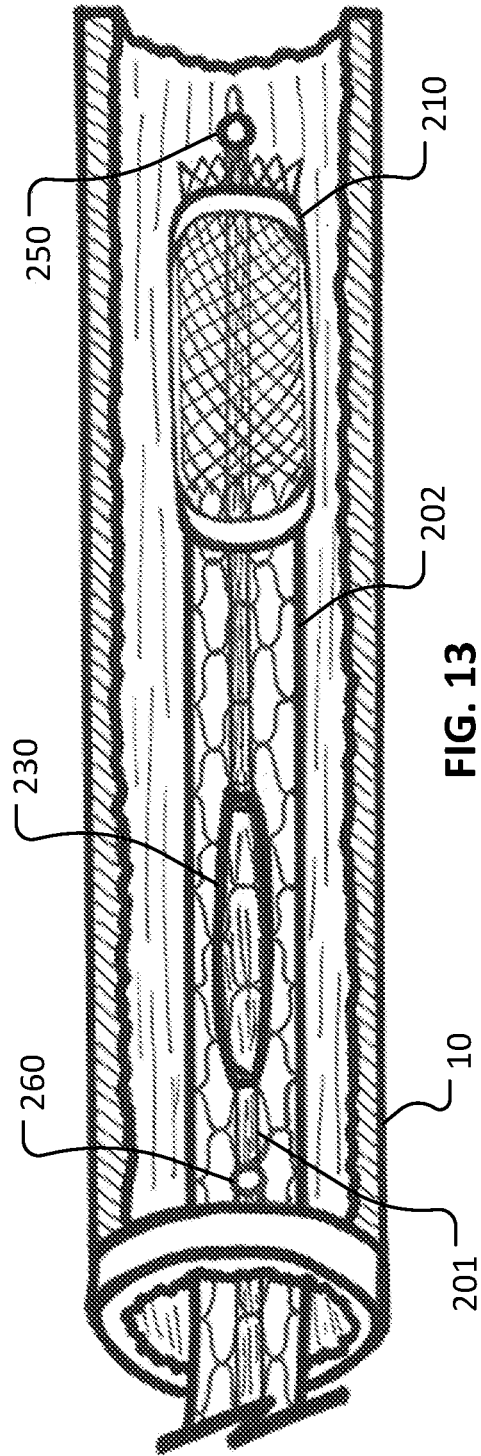

1

AUTOMATED RETRIEVABLE HEMORRHAGE CONTROL SYSTEM

CROSS-REFERENCE TO RELATED APPLICATIONS

This application is a continuation application of U.S. application Ser. No. 15/556,922, filed on Sep. 8, 2017, which is a National Stage application under 35 U.S.C. § 371 of International Application No. PCT/US2016/021728, filed on Mar. 10, 2016, which claims the benefit of U.S. Patent Application Ser. No. 62/131,574, filed Mar. 11, 2015, and 62/162,966, filed on May 18, 2015, the contents of these prior applications being fully incorporated herein by reference.

TECHNICAL FIELD

This document relates to devices, systems, and methods for controlling catastrophic bleeding from large and medium size vessels such as, but not limited to, the aorta or iliac arteries.

BACKGROUND

Injuries in the United States account for roughly 51% of all deaths among persons 1-44 years of age, which is more than all non-communicable and infectious diseases combined. Exsanguinating non-compressible hemorrhage, mainly from the aorta and its branches, is a major contributor to these mortalities. Causes of such catastrophic bleeding that require the rapid cessation of hemorrhaging vessels include but are not limited to: high-speed motor vehicle accidents, falls from heights, crush injuries, explosions, and gunshot wounds. Many instances of a non-compressible hemorrhage could effectively be controlled with Resuscitative Endovascular Balloon Occlusion of the Aorta (REBOA). REBOA often encompasses vascular access through a non-injured artery in the leg or arm, fluoroscopy-guided navigation and deployment of an occlusion balloon proximal to the site of injury. However, complete occlusion of the aorta for prolonged periods of time may result in permanent damage or injury to downstream organs and tissues that are not perfused with blood.

SUMMARY

Some embodiments of an endovascular device are configured to intravascularly control non-compressible bleeding through a blood vessel while preserving blood flow to organs and tissues that are downstream from the site of the injury. In particular embodiments, the endovascular device includes a stent graft comprising an expandable tubular metallic frame and a covering material disposed on at least a portion of the metallic frame. The stent graft defines a lumen that extends between a first end of the stent graft and a second end of the stent graft. In some embodiments, one or multiple balloons are disposed around an outer periphery of the stent graft. In particular embodiments, two outer periphery balloons are spaced apart from each other. In various embodiments, an additional balloon is disposed within the lumen at a location along the stent graft. This additional balloon can have an inflated configuration that is controllable for fully and/or partially occluding the lumen. In additional embodiments, the stent graft can be integrated with greater and/or fewer balloons along the outer periphery and/or within the lumen to control blood flow within the targeted vessel. In some embodiments, the endovascular device includes one or more sensors and a control unit. The sensor(s) and control unit can automate functions of the endovascular device including a diagnosis function and a bleeding reduction function. Accordingly, in some circumstances, endovascular devices provided herein are configured for use in the aorta and/or other blood vessels to endovascularly control the non-compressible bleeding of a patient while preserving and/or controlling the blood flow to organs and tissues that are downstream from the site of injury.

In one implementation an endovascular device includes a stent graft comprising an expandable tubular metallic frame and a covering material disposed on at least a portion of the metallic frame. The stent graft defines a lumen that extends between a first end of the stent graft and a second end of the stent graft. The endovascular device also includes a first balloon disposed around an outer periphery of the stent graft, a second balloon disposed around the outer periphery of the stent graft and spaced apart from the first balloon, and a third balloon disposed within the lumen at a location along the stent graft between the first balloon and the second balloon. The third balloon has a fully inflated configuration that fully occludes the lumen and a partially inflated configuration that partially occludes the lumen for modulating blood flow through the stent graft.

Such an endovascular device may optionally include one or more of the following features. The first balloon may fully surround the outer periphery of the stent graft. The second balloon may fully surround the outer periphery of the stent graft. The endovascular device may also include a fourth balloon disposed around the outer periphery of the stent graft and spaced apart from the first and second balloons. The endovascular may also include a fifth balloon disposed around the outer periphery of the stent graft and spaced apart from the first, second, and fourth balloons. The endovascular device may also include a first sensor coupled to the stent graft. The first sensor may be configured to detect fluid pressure or blood flow rate. The endovascular device may also include a second sensor coupled to the stent graft. The second sensor may be configured to detect fluid pressure or blood flow rate. The first sensor may be located distally of the third balloon and the second sensor may be located proximally of the third balloon. The metallic frame may comprise nitinol. The stent graft may be self-expanding. At least a portion of the stent graft may be diametrically tapered along a longitudinal length of the stent graft. In some embodiments, at least a portion of the metallic frame is not covered by the covering material. In particular embodiments, an end portion of the metallic frame is not covered by the covering material. In various embodiments, a middle portion of the stent graft includes one or more open areas that are not covered by the covering material, and portions of the stent graft immediately adjacent on each side of the one or more open areas are covered by the covering material. In some embodiments, each of the first, second, and third balloons may be inflatable independent of each other via one or more catheters coupled to the stent graft. The endovascular device may further comprise at least one sensor coupled to the stent graft and be configured for detecting blood gases. The endovascular device may also include at least one sensor coupled to the stent graft and configured for detecting pH.

In another implementation, a system for controlling catastrophic bleeding from vessels includes an endovascular device and a control unit coupleable to the endovascular device. The endovascular device includes a stent graft comprising an expandable tubular metallic frame and a covering material disposed on at least a portion of the metallic frame, the stent graft defining a lumen that extends between a first end of the stent graft and a second end of the stent graft, a first balloon disposed around an outer periphery of the stent graft, a second balloon disposed around the outer periphery of the stent graft and spaced apart from the first balloon, and a third balloon disposed within the lumen at a location along the stent graft between the first balloon and the second balloon. The third balloon has a fully inflated configuration that fully occludes the lumen and a partially inflated configuration that partially occludes the lumen for modulating blood flow through the stent graft. The control unit is coupleable to the endovascular device and configured for delivering inflation media to at least one of the first, second, and third balloons.

Such a system for controlling catastrophic bleeding from vessels may optionally include one or more of the following features. The system may also include a first sensor coupled to the stent graft. The first sensor may be configured to detect fluid pressure or blood flow rate. The system may also include a second sensor coupled to the stent graft. The second sensor may be configured to detect fluid pressure or blood flow rate. The first sensor may be located distally of the third balloon and the second sensor may be located proximally of the third balloon. The control unit may be configured to receive signals indicative of fluid pressure or blood flow rate from each of the first sensor and the second sensor. The control unit may be configured to control a delivery of inflation media to one or more of the first, second, and third balloons based on one or more of the signals indicative of fluid pressure of blood flow rate.

In another implementation, a method for controlling catastrophic bleeding from vessels includes deploying an endovascular device in a blood vessel. The endovascular device includes a stent graft comprising an expandable tubular metallic frame and a covering material disposed on at least a portion of the metallic frame. The stent graft defines a lumen that extends between a first end of the stent graft and a second end of the stent graft. The endovascular device also includes a first balloon disposed around an outer periphery of the stent graft, a second balloon disposed around the outer periphery of the stent graft and spaced apart from the first balloon, and a third balloon disposed within the lumen at a location along the stent graft between the first balloon and the second balloon, the third balloon having a fully inflated configuration that fully occludes the lumen and a partially inflated configuration that partially occludes the lumen for modulating blood flow through the stent graft.

Such a method for controlling catastrophic bleeding from vessels may optionally include one or more of the following features. The method may also include inflating at least one of the first balloon and the second balloon such that blood in the blood vessel flows in the lumen rather than flowing between the at least one of the first balloon and the second balloon and a wall of the blood vessel. The method may also include coupling a control unit to the endovascular device. The control unit may be configured for delivering inflation media to at least one of the first, second, and third balloons via one or more catheters coupled to the stent graft. The control unit may perform the inflating at least one of the first balloon and the second balloon. The control unit may perform the inflating in response to one or more blood pressure signals from one or more sensors coupled to the stent graft.

In another implementation, an endovascular device includes a stent graft, a first balloon disposed around an outer periphery of the stent graft, and a second balloon disposed around the outer periphery of the stent graft and spaced apart from the first balloon.

Such an endovascular device may optionally include one or more of the following features. The endovascular device may also include a third balloon disposed within a lumen defined by the stent graft at a location along the stent graft between the first balloon and the second balloon. The third balloon may have a fully inflated configuration that fully occludes the lumen and a partially inflated configuration that partially occludes the lumen for modulating blood flow through the stent graft.

Some or all of the embodiments described herein may provide one or more of the following advantages. First, in some cases catastrophic bleeding can be controlled using the devices, systems, and methods provided herein. Moreover, some embodiments can be advantageously used to detect and precisely isolate the location of bleeding. For example, some embodiments can serve both as an endovascular intracorporeal-vascular shunt to redirect or distribute blood flow as well as a complete occlusion device to aid in the localization and rapid cessation of a non-compressible hemorrhage.

Second, in some optional embodiments, a computerized control unit of the system can deploy the stent graft and balloons in response to hemodynamic parameters detected by one or more sensors coupled to the stent graft. In that manner, the stent graft and balloons can selectively isolate segments of the vessel to stop or slow hemorrhage, and can do so while reducing the potential for human errors. In addition, in some embodiments the one or more sensors can sense pressure and/or blood flow difference(s) within the vasculature to determine the location of bleeding and, in response, the control unit can inflate and/or deflate balloons to re-establish blood flow to unaffected areas. In doing so, the system reduces blood loss through the injured vessel while maintaining its integrity to nourish the downstream organs and tissues. Hence, better patient outcomes can be achieved.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 9 is a transverse cross-sectional view of a blood vessel showing a distal end view of the endovascular device of FIG. 4 with deflated internal and external balloons.

FIG. 10 is a transverse cross-sectional view of a blood vessel showing a distal end view of the endovascular device of FIG. 4 with an inflated external balloon and a deflated internal balloon.

FIG. 11 is a transverse cross-sectional view of a blood vessel showing a distal end view of the endovascular device of FIG. 4 with inflated internal and external balloons.

FIG. 12 is a transverse cross-sectional view of a blood vessel showing a distal end view of the endovascular device of FIG. 4 that includes a first example stent construct.

FIG. 13 is a transverse cross-sectional view of a blood vessel showing a distal end view of the endovascular device of FIG. 4 that includes a second example stent construct.

Like reference symbols in the various drawings indicate like elements.

DETAILED DESCRIPTION OF ILLUSTRATIVE EMBODIMENTS

Figure 1:
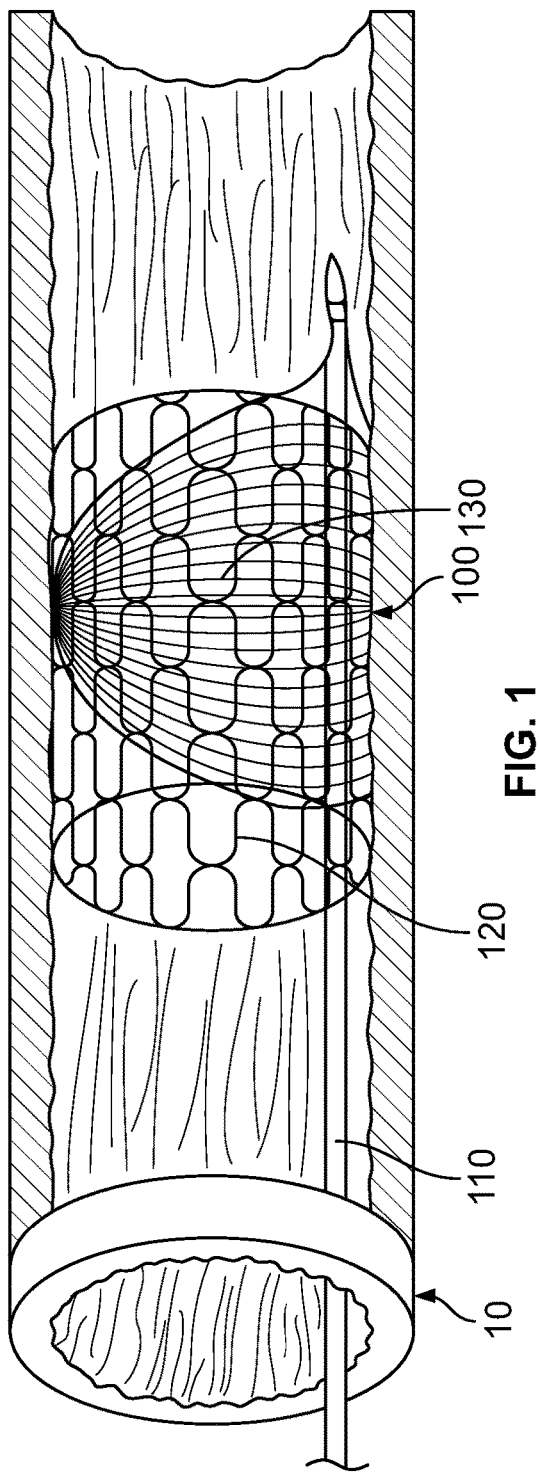
FIG. 1 is a partial longitudinal cross-sectional view of a blood vessel containing an example stent graft with an internal balloon in accordance with some embodiments.
Figure 3:
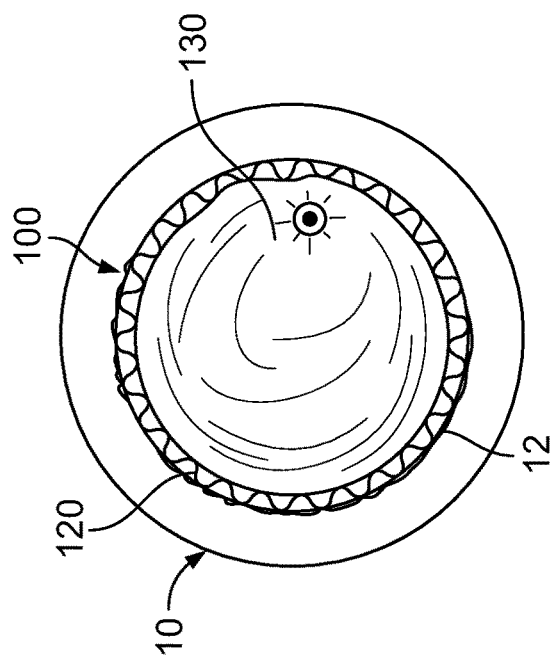
FIG. 3 is a transverse cross-sectional view of the arrangement of FIG. 1 with the stent graft and balloon in diametrically expanded configurations.
Figure 2:
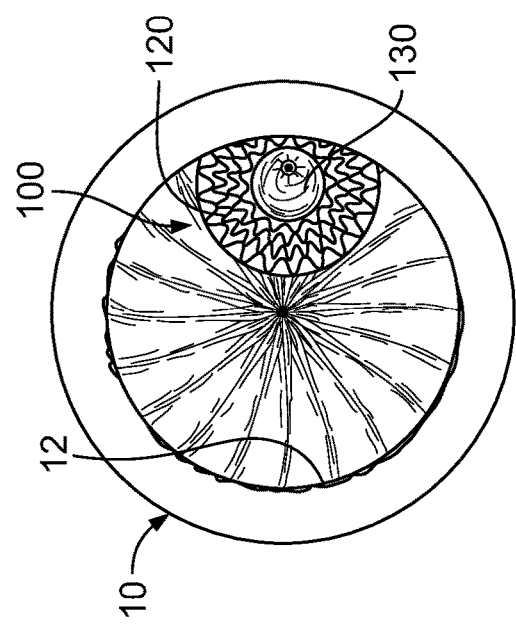
FIG. 2 is a transverse cross-sectional view of the arrangement of FIG. 1 with the stent graft and balloon in diametrically contracted configurations.

Referring to FIGS. 1-3, some embodiments of a stent graft device 100 are configured for deployment in a blood vessel 10, such as in the aorta, other arterial vessels, and/or venous vessels. In some embodiments, as described further below, the stent graft device 100 can allow precise control of the blood flow through blood vessel 10.

The stent graft device 100 includes a catheter 110, a stent 120, and a balloon 130. The catheter 110 is coupled to the stent 120 and/or to the balloon 130. The catheter 110 includes at least one lumen through which inflation media (e.g., liquid or gas) can be passed to inflate and/or deflate the balloon 130. At least a portion of the balloon 130 is located within the interior of the stent 120. In the depicted embodiment, a majority of the balloon 130 is located within the interior of the stent 120.

The stent graft device 100 is expandable between a low-profile configuration and a diametrically expanded, deployed configuration. For example, FIG. 2 shows the stent graft device 100 in a low-profile configuration, and FIGS. 1 and 3 show the stent graft device 100 in a diametrically expanded, deployed configuration. In the diametrically expanded, deployed configuration an outer periphery of the stent 120 is in contact with an inner wall surface 12 of the blood vessel.

In some embodiments, the stent graft device 100 can be deployed into the vasculature (e.g., blood vessel 10) using a delivery sheath. With the balloon 130 fully deflated, the stent graft device 100 can be diametrically compressed into the low-profile configuration for containment within a lumen of the delivery sheath. A distal portion of the delivery sheath containing the stent graft device 100 can be passed into the patient's vasculature via a percutaneous access site such as, but not limited to, a femoral artery, a radial artery, a subclavian artery, and the like. The approach can be retrograde or antegrade. In some embodiments, the delivery sheath can be navigated within the vasculature using one or more imaging modalities such as, but not limited to, x-ray fluoroscopy, ultrasound, and the like. In some embodiments, a guidewire may be placed within the vasculature first and the delivery sheath can be deployed over the guidewire.

When the stent graft device 100 (within the delivery sheath) is positioned at a target location in the vasculature, the delivery sheath can be pulled back while the position of the catheter 110 is maintained substantially stationary. Alternatively, or additionally, the catheter 110 can be advanced distally in relation to the delivery sheath. Such relative motions of the catheter 110 and the delivery sheath can cause the stent graft device 100 to be expressed from the delivery sheath at the target site.

In some embodiments, the stent 120 will self-expand to the deployed configuration such that the outer periphery of the stent 120 is in contact with the inner wall surface 12 of the blood vessel 10. Alternatively, or additionally, in some embodiments, the balloon 130 (or another balloon) can be used to expand the stent 120 such that the outer periphery of the stent 120 is in contact with the inner wall surface 12 of the blood vessel 10. While the stent 120 is in contact with the inner wall surface 12 of the blood vessel, the stent graft device 100 is temporarily anchored in relation to the blood vessel 10.

The stent graft device 100 is retrievable from the patient's vasculature. That is, the stent graft device 100 can be recaptured into a sheath and then the sheath containing the stent can be removed from the patient's vasculature. Hence, the stent graft device 100 is configured to be temporarily implanted.

The catheter 110 is an elongate flexible member that defines at least one lumen (for carrying inflation media). The catheter 110 can comprise a tubular polymeric or metallic material. For example, in some embodiments the catheter 110 can be made from polymeric materials such as, but not limited to, polytetrafluoroethylene (PTFE), fluorinated ethylene propylene (FEP), HYTREL®, nylon, PICOFLEX®, PEBAX®, TECOFLEX®, and the like, and combinations thereof. In alternative embodiments, the catheter 110, or portions thereof, can be made from metallic materials such as, but not limited to, nitinol, stainless steel, stainless steel alloys, titanium, titanium alloys, and the like, and combinations thereof. In some embodiments, the catheter 110 can be made from combinations of such polymeric and metallic materials (e.g., polymer layers with metal braid, coil reinforcement, stiffening members, and the like, and combinations thereof). In particular embodiments, some longitudinal portions of the catheter 110 may be configured to have different mechanical properties than other longitudinal portions of the catheter 110. For example, some portions may be stiffer, more lubricious, have greater column strength, may be more flexible, may have a smaller or larger diameter, and the like, as compared to other portions of the catheter 110. In some embodiments, one or more radiopaque markers can be located on the catheter 110.

The stent 120 is made of one or more elongate members. In some embodiments, the elongate members of the stent 120, are formed from a single piece of precursor material (e.g., sheet or tube) that is cut, expanded, and then shape-set in the expanded configuration. For example, some embodiments are fabricated from a tube that is laser-cut (or machined, chemically etched, water-jet cut, etc.) and then expanded and heat-set into its final expanded size and shape. In some embodiments, the stent 120 is created compositely from multiple elongate members (e.g., wires or cut members) that are joined together to form the stent 120. In some embodiments, the stent 120 is made of one or more wires that is/are braided or woven to form a mesh-like structure.

The elongate members of the stent 120 can be comprised of various materials and combinations of materials. In some embodiments, nitinol (NiTi) is used as the material of the elongate members of the stent 120, but other materials such as stainless steel, L605 steel, polymers, MP35N steel, stainless steels, titanium, cobalt/chromium alloy, polymeric materials, Pyhnox, Elgiloy, or any other appropriate biocompatible material, and combinations thereof can be used. The super-elastic properties of NiTi make it a particularly good candidate material for the elongate members of the stent 120 because, for example, NiTi can be heat-set into a desired shape. That is, NiTi can be heat-set so that the stent 120 tends to self-expand into a desired shape when the stent 120 is unconstrained, such as when the stent 120 is deployed out from the delivery sheath. A stent 120 made of NiTi, for example, may have a spring nature that allows the stent 120 to be elastically collapsed or "crushed" to a low-profile delivery configuration as shown in FIG. 2, and then to reconfigure to the expanded configuration as shown in FIGS. 1 and 3. The stent 120 may be conformable, fatigue resistant, and elastic such that the stent 120 can conform to the topography of the surrounding vasculature when the stent 120 is deployed in a vessel 10 of a patient.

In some embodiments, the diameter or width/thickness of one or more of the elongate members forming the stent 120 may be within a range of about 0.008" to about 0.015" (about 0.20 mm to about 0.40 mm), or about 0.009" to about 0.030" (about 0.23 mm to about 0.76 mm), or about 0.01" to about 0.06" (about 0.25 mm to about 1.52 mm), or about 0.02" to about 0.10" (about 0.51 mm to about 2.54 mm), or about 0.06" to about 0.20" (about 1.52 mm to about 5.08 mm). In some embodiments, the elongate members forming the stent 120 may have smaller or larger diameters or widths/thicknesses. In some embodiments, each of the elongate members forming the stent 120 has essentially the same diameter or width/thickness. In some embodiments, one or more of the elongate members forming the stent 120 has a different diameter or width/thickness than one or more of the other elongate members of the stent 120. In some embodiments, one or more portions of one or more of the elongate members forming the stent 120 may be tapered, widened, narrowed, curved, radiused, wavy, spiraled, angled, and/or otherwise non-linear and/or not consistent along the entire length of the elongate members of the stent 120.

In some embodiments, the stent 120 includes one or more eyelets or other types of attachment features. In particular embodiments, the stent 120 includes a lasso-like member threaded through multiple portions of the stent 120 such that the stent 120 can be cinched to a smaller diameter by tensioning the lasso member to assist in retrieval of the stent 120. One or more radiopaque markers may be included on some embodiments of the stent 120.

In some embodiments, the stent 120 includes a covering material on at least a portion of the stent 120, or on the entire stent 120. Hence, in some cases the stent 120 may be referred to as a stent graft device 120. It should be understood, that such a covering material is optional. That is, in some embodiments the stent 120 is a bare stent. The covering material may provide enhanced sealing between the stent 120 and the vessel wall 12 in some cases. In some embodiments, two or more portions of covering material, which can be separated and/or distinct from each other, can be disposed on the stent 120. That is, in some embodiments a particular type of covering material is disposed on some areas of the stent 120 and a different type of covering material is disposed on other areas of the stent 120.

In some embodiments, the covering material, or portions thereof, comprises a hydrophobic fluoropolymer, such as an expanded polytetrafluoroethylene (ePTFE) polymer. In some embodiments, the covering material, or portions thereof, comprises a polyester, a silicone, a urethane, ELAST-EON™ (a silicone and urethane polymer), another biocompatible polymer, DACRON®, polyethylene terephthalate (PET), copolymers, or combinations and subcombinations thereof. In some embodiments, the covering material is manufactured using techniques such as, but not limited to, electrospinning, extrusion, expansion, heat-treating, sintering, knitting, braiding, weaving, chemically treating, and the like. In some embodiments, the covering material, or portions thereof, comprises a biological tissue. For example, in some embodiments the covering material can include natural tissues such as, but not limited to, bovine, porcine, ovine, or equine pericardium. In some such embodiments, the tissues are chemically treated using glutaraldehyde, formaldehyde, or triglycidylamine (TGA) solutions, or other suitable tissue crosslinking agents.

In some embodiments, the covering material is disposed on the interior and the exterior of the framework of the stent 120. In some embodiments, the covering material is disposed on the just the exterior of the framework of the stent 120. In some embodiments, the covering material is disposed on the just the interior of the framework of the stent 120. In some embodiments, some portions of the framework of the stent 120 are covered by the covering material in a different manner than other portions of the framework of the stent 120.

In some embodiments, the covering material is attached to at least some portions of the framework of the stent 120 using an adhesive. In some embodiments, epoxy is used as an adhesive to attach the covering material to the framework of the stent 120, or portions thereof. In some embodiments, wrapping, stitching, lashing, banding, and/or clips, and the like can be used to attach the covering material to the framework of the stent 120. In some embodiments, a combination of techniques is used to attach the covering material to the framework of the stent 120.

The stent graft device 100 also includes the balloon 130. In some embodiments, the balloon 130 is made of silicone. But materials such as, but not limited to, latex, fluoroelastomers, polyurethane, polyethylene terephthalate (PET), and the like, are used in some embodiments.

The balloon 130 can be inflated to fully occlude the interior of the stent 120. In such a case, essentially no blood will be allowed to flow through the stent 120. The balloon 130 can also be deflated to a very small size such that it only minimally impedes blood flow through the stent 120.

Further, the balloon 130 can be selectively inflated to a partially inflated configuration such that the balloon 130 partially occludes the interior of the stent 120. That is, the size of the balloon 130 can be adjusted by a clinician, or an automated control unit (described further below), by selectively filling the balloon 130 with an amount of inflation media (e.g., saline, $CO_2$, etc.) that only partially fills the capacity of the balloon 130. In that manner, the extent of occlusion of the stent 120 by the partially inflated balloon 130 can be selected/controlled, and therefore the amount of blood flow through the stent 120 can be modulated.

Figure 4:
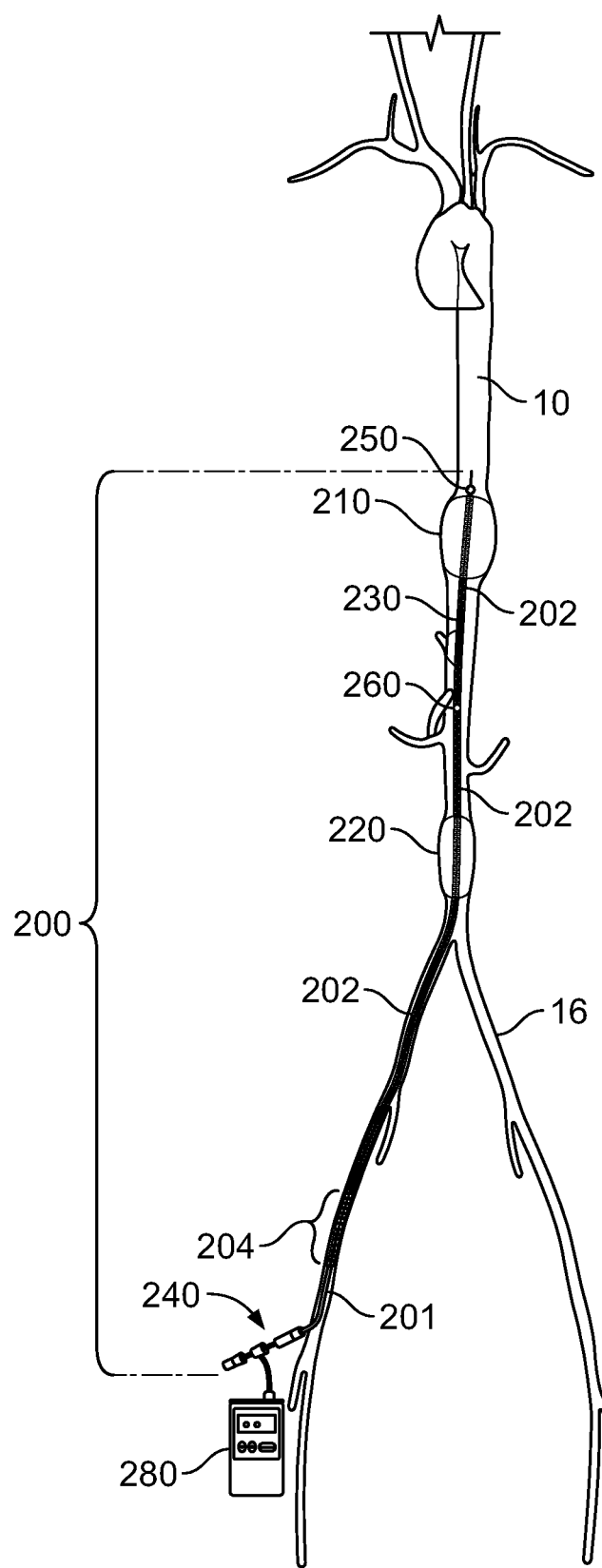
FIG. 4 is an illustration of a portion of a human vasculature, including an aorta and its branches, containing an example endovascular device with one internal and two external balloons coupled to a control unit in accordance with some embodiments.

Referring to FIG. 4, some embodiments of an endovascular stent graft device 200 can be configured for deployment in a blood vessel 10, whereat the endovascular stent graft device 200 can be operated in a manner that reduces blood loss through an injured vessel while allowing blood flow to downstream organs and tissues.

The endovascular stent graft device 200 includes a catheter 201, a stent graft 202, a first balloon 210, a second balloon 220, a third balloon 230, a catheter hub 240, a first sensor 250, and a second sensor 260. In some embodiments, a control unit 280 is coupleable to the endovascular stent graft device 200 to comprise a system for controlling catastrophic bleeding from blood vessels.

The stent graft 202 defines a lumen that extends between the ends of the stent graft 202 (between the proximal and distal ends which are open). The catheter 201 is coupled to the catheter hub 240 and to the stent graft 202. The first balloon 210 and the second balloon 220 are coupled around an outer periphery of the stent graft 202. As such, the first balloon 210 and the second balloon 220 do not occlude the lumen of the stent graft 202. The third balloon 230 is disposed within the lumen of the stent graft 202. Therefore, when the third balloon 230 is inflated, the third balloon 230 can occlude the lumen of the stent graft 202 (e.g., like the balloon 130 of stent graft device 100 described above in reference to FIGS. 1-3). Depending on the extent of inflation (as controlled by the clinician or control unit 280), the third balloon 230 can either partially or fully occlude the lumen of stent graft 202. The catheter hub 240 is coupleable to the control unit 280.

The endovascular stent graft device 200 is expandable between a low-profile configuration and a diametrically expanded, deployed configuration. FIG. 4 shows the endovascular stent graft device 200 in the diametrically expanded, deployed configuration. In the deployed configuration, some portions of the stent graft 202 may make full peripheral contact with the inner wall surface of the vessel 10, while some other portions may not make full peripheral contact with the inner wall surface of the vessel 10. In some embodiments, the endovascular stent graft device 200 can be deployed into the vasculature (e.g., blood vessel 10) using a delivery sheath.

A distal portion of the delivery sheath containing the endovascular stent graft device 200 can be passed into the patient's vasculature via a percutaneous access site such as, but not limited to, a femoral artery (as shown in FIG. 4), femoral vein, a radial artery, a subclavian artery, and the like. The approach can be retrograde or antegrade. In some embodiments, the delivery sheath can be navigated within the vasculature using one or more imaging modalities such as, but not limited to, x-ray fluoroscopy, ultrasound, and the like. In some embodiments, a guidewire may be placed within the vasculature first and the delivery sheath can be deployed over the guidewire.

While the endovascular stent graft device 200 is depicted as being deployed within an aorta (blood vessel 10), it should be understood that other vessels may be treated using the endovascular stent graft device 200. That is, the endovascular stent graft device 200 is scalable to smaller sizes for use in other areas of a patient's vasculature. Moreover, the endovascular stent graft device 200 can be used to treat venous bleeding (such as retrohepatic vena cava injuries), pelvic hemorrhages or fractures, and uterine or gastrointestinal bleeding, to provide a few examples.

When the endovascular stent graft device 200 (within the delivery sheath) is positioned at a target location in the vasculature, the delivery sheath can be pulled back while the position of the catheter 201 is maintained substantially stationary. Alternatively, or additionally, the catheter 201 can be advanced distally in relation to the delivery sheath. Such relative motions of the catheter 201 and the delivery sheath can cause the endovascular stent graft device 200 to be expressed from the delivery sheath at the target site.

In some embodiments, the stent graft 202 will self-expand to the deployed configuration. Alternatively, or additionally, in some embodiments, one or more balloons can be used to expand some or all of the stent graft 202. While the stent graft 202 is deployed and in the expanded configuration inside of the blood vessel 10, in some cases the endovascular stent graft device 200 is temporarily anchored in relation to the blood vessel 10.

The endovascular stent graft device 200 is retrievable from the patient's vasculature. That is, the endovascular stent graft device 200 can be recaptured into a sheath and then the sheath containing the stent graft device 200 can be removed from the patient's vasculature. Hence, the endovascular stent graft device 200 is configured to be temporarily implanted.

In some embodiments, the catheter 201 includes multiple lumens through which inflation media (e.g., liquid or gas) can be passed, to individually and independently inflate and deflate the balloons 210, 220, and 230 (and any additional balloons that are included in some embodiments but not depicted herein). The catheter 210 can be made of any of the materials described above in reference to catheter 110. In some embodiments, rather than using a single multi-lumen catheter 201, two or more separate catheters may be included with lumens for supplying inflation media to the balloons 210, 220, and/or 230 (and other balloons if so configured).

In some embodiments, the stent graft 202 is an elongate stent graft comprising an expandable tubular metallic frame and a covering material disposed on at least a portion of the metallic frame. The stent graft 202 (e.g., the elongate members and covering material) can be made of any of the materials described above in reference to stent 120.

The first and second balloons 210 and 220 are disposed around the outer periphery of the stent graft 202. The first and second balloons 210 and 220 are spaced apart from each other (with the third balloon 230 disposed between the first and second balloons 210 and 220). The first and second balloons 210 and 220 can be inflated such that the outer peripheries of the first and second balloons 210 and 220 make full peripheral contact with the inner wall surface of the vessel 10. Hence, while the first and second balloons 210 and 220 are inflated, a seal between the first and second balloons 210 and 220 and the vessel 10 is created. Therefore, blood flowing through the vessel 10 will be directed (shunted) into the lumen of the stent graft 202 while the first and second balloons 210 and 220 are inflated and in full peripheral contact with the inner wall surface of the vessel 10.

The third balloon 230 is disposed within the lumen of the stent graft 202. The third balloon 230 can be inflated to fully occlude the interior of the stent graft 202. In such a case, essentially no blood will be allowed to flow through the lumen of the stent graft 202. In addition, the third balloon 230 can be partially inflated to partially occlude the interior lumen of the stent graft 202. Hence, the extent of inflation of the third balloon can be selectively controlled to modulate the blood flow through the lumen of the stent graft 202. The third balloon 230 can also be deflated to a very small size such that it only minimally impedes blood flow through the lumen of the stent graft 202.

The balloons 210, 220, and 230 (and/or any additional balloons included but not depicted in the figures) can be made of any of the materials described above in reference to balloon 130.

Again, the third balloon 230 can be selectively inflated to a partially inflated configuration such that the third balloon 230 partially occludes the interior of the stent graft 202. That is, the size of the third balloon 230 can be adjusted by a clinician, or by the automated control unit 280, by selectively filling the third balloon 230 with an amount of inflation media (e.g., saline, $CO_2$, etc.) that only partially fills the capacity of the third balloon 230. In that manner, the extent of occlusion of the lumen of the stent graft 202 by the partially inflated third balloon 230 can be selected/controlled, and therefore the amount of blood flow through the lumen of the stent graft 202 can be modulated.

Figure 7:
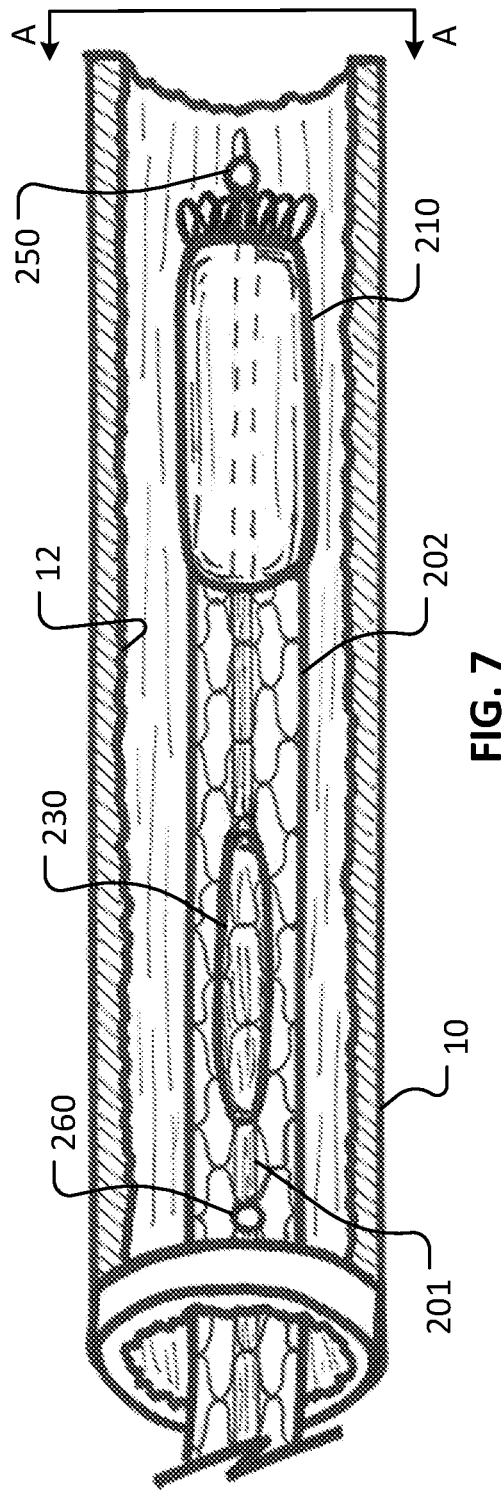
FIG. 7 is a partial longitudinal cross-sectional view of a blood vessel containing the distal end portion of the example endovascular device of FIG. 4 with deflated balloons.

Referring also to FIG. 7, the distal end portion of endovascular stent graft device 200 is shown within the vessel 10. The depicted distal end portion of endovascular stent graft device 200 includes the stent graft 202, the first balloon 210 disposed around the exterior of the stent graft 202, and the third balloon 230 disposed within the interior lumen of the stent graft 202. The catheter 201 and sensors 250 and 260 are also shown. The second balloon 220 (since it is located proximal to the third balloon 230) is not visible in this view of the distal end portion of endovascular stent graft device 200.

In the depicted configuration, both the first balloon 210 and the third balloon 230 are deflated. This configuration would allow blood to flow around the first balloon 210 (between the exterior surface of the first balloon 210 and the inner wall 12 of the vessel 10) because the first balloon 210 is not in contact with the inner wall 12. In addition, this configuration would allow blood to flow through the lumen of the stent graft 202 because the exterior surface of the third balloon 230 is not in contact with the inner wall of the stent graft 202.

Figure 8:
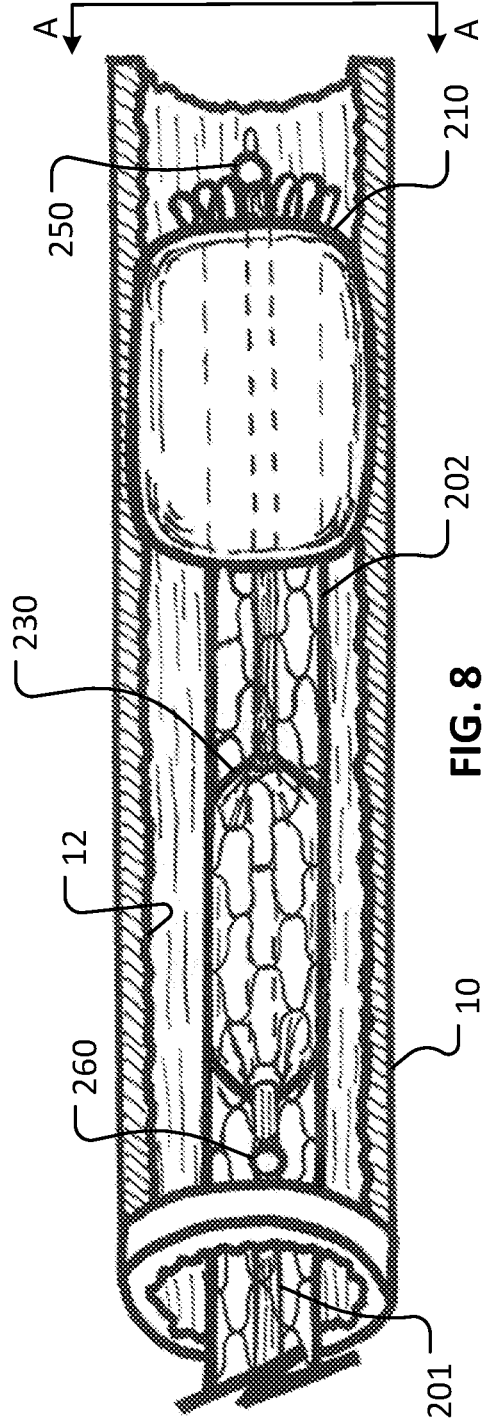
FIG. 8 is a partial longitudinal cross-sectional view of a blood vessel containing the distal end portion of the example endovascular device of FIG. 4 with inflated balloons.

Referring also to FIG. 8, again the distal end portion of endovascular stent graft device 200 is shown within the vessel 10. In the depicted configuration, both the first balloon 210 and the third balloon 230 are inflated. This configuration would block blood from flowing through the vessel 10, and block blood from flowing through the lumen of the stent graft 202. That is, with the first balloon 210 inflated such that the exterior surface of the first balloon 210 is in contact with the inner wall 12 of the vessel 10, blood is blocked from flowing therebetween. The inflated first balloon 210 (being disposed around the exterior of the stent graft 202) does not block the lumen of the stent graft 202. However, that said, in the depicted configuration the third balloon 230 is also inflated. Therefore, blood is blocked from flowing through the lumen of the stent graft 202 because the exterior surface of the third balloon 230 is in contact with the inner wall of the stent graft 202. In other words, in the depicted configuration the third balloon 230 is inflated so as to fully occlude the lumen of the stent graft 202. In should be understood that in some cases the third balloon 230 can be partially inflated to modulate the flow of blood through the lumen of the stent graft 202.

Referring also to FIGS. 9-11, distal end views (as viewed from vantage point A-A shown in FIGS. 7 and 8) of the endovascular stent graft device 200 are depicted to illustrate the endovascular stent graft device 200 in various configurations.

In FIG. 9, both the first balloon 210 and the third balloon 230 are deflated. Hence, blood can flow between the exterior surface of the first balloon 210 and the inner wall 12 of the vessel 10. Additionally, blood can flow between the exterior surface of the third balloon 230 and the inner wall of the stent graft 202. This arrangement is like that of FIG. 7.

In FIG. 10, the first balloon 210 is inflated such that its exterior surface is in contact with the inner wall 12 of the vessel 10, but the third balloon 230 is deflated (or at least partially deflated). Hence, blood is blocked from flowing between the first balloon 210 and the inner wall 12 of the vessel 10. However, the inflation of the first balloon 210 does not prevent blood from flowing into the lumen of the stent graft 202. Moreover, since the exterior surface of the third balloon 230 is not in contact with the inner wall of the stent graft 202, the third balloon 230 is not fully occluding blood from flowing through the lumen of the stent graft 202. That is, in the depicted configuration blood is allowed to flow within the lumen of the stent graft 202 because neither the first balloon 210 nor the third balloon 230 is fully occluding the lumen of the stent graft 202. It can be said that the configuration of FIG. 10 allows blood to be shunted from the vessel 10 using the lumen of the stent graft 202.

In FIG. 11, both the first balloon 210 and the third balloon 230 are inflated. Hence, blood cannot flow between the exterior surface of the first balloon 210 and the inner wall 12 of the vessel 10. Additionally, blood cannot flow between the exterior surface of the third balloon 230 and the inner wall of the stent graft 202. This arrangement is like that of FIG. 8.

Referring again to FIG. 4, the endovascular stent graft device 200 also includes the catheter hub 240. The catheter hub 240 provides individual end ports for the multiple lumens of the catheter 210. In some embodiments, the catheter hub 240 may be configured for attachment with one or more mating members, such as attachment to the control unit 280.

In some embodiments, the endovascular stent graft device 200 also includes the first sensor 250 and/or the second sensor 260 (see also FIGS. 12 and 13). The sensors 250 and 260 are optional. The sensors 250 and 260 can be various types of sensors. Each of the sensors 250 and 260 can represent one or more actual detection devices for detecting one or more different parameters. For example, in some embodiments, one or both of the sensors 250 and 260 can detect fluid pressure and/or flow (but not any other parameters). In some embodiments, one or both of the sensors 250 and 260 can detect two or more parameters. Such parameters can include, but are not limited to, fluid pressure, flow rate, blood gases (e.g., $O_2$, $CO_2$, etc.), temperature, pH, heart rate, and the like.

The sensors 250 and 260 can be located at any positions along the stent graft 202. In the depicted embodiment, the sensor 250 is located distal of the first balloon 210, and the second sensor 260 is located between the second balloon 220 and the third balloon 230. In some embodiments, more than two sensors are included (and such sensors can be located at any position(s) along the stent graft 202).

The sensors 250 and 260 can be in communication with the control unit 280 such that one or more signals from the sensors 250 and 260 are received by the control unit. In some embodiments, the sensors 250 and 260 may be in communication with one or more other monitoring devices.

The optional control unit 280 can be coupled with the catheter hub 240 in some embodiments. The control unit 280 can provide computerized (automatic or semi-automatic) control of the endovascular stent graft device 200. That is, the control unit 280 can individually inflate and/or deflate balloons 210, 220, and 230 to selectively isolate segments of the vessel 10 to diagnose the location of a hemorrhage and to stop or slow hemorrhage. Moreover, the sensors 250 and 260 can sense pressure and/or flow differences within the vessel 10 to determine or diagnose the location of bleeding and re-establish blood flow to unaffected areas. In doing so, the control unit 280 in conjunction with the endovascular stent graft device 200 can reduce blood loss through the injured vessel 10 while maintaining its integrity to nourish the downstream organs and tissues. The external computerized control unit 280 consists of hardware and software that are integrated with the catheter sensors 250 and 260 and an effector system that can rapidly inflate or deflate the balloons 210, 220, and 230 (individually) with liquid or gaseous inflation media.

The control unit 280 in conjunction with the endovascular stent graft device 200 can sense and precisely isolate the area of injury while preserving blood flow to critical downstream organs and tissues. This can serve both as an endovascular intracorporeal-vascular shunt as well as a complete occlusion device to aid in the localization and rapid cessation of a non-compressible hemorrhage.

In some embodiments, one or more additional balloons (configured like balloons 210 and 220) can be located on the stent graft 202. In such a case, the particular balloons selected for use can be made based on the size of the vessel (or size of the patient) and the patient's particular arterial branching locations. Said differently, by including one or more additional balloons (configured like balloons 210 and 220) located on the stent graft 202, the endovascular stent graft device 200 can be more of a one-size-fits-all device.

In some embodiments, the stent graft 202 includes an uncovered portion 204. Such an uncovered portion 204 can make for easier retrieval of the endovascular stent graft device 200 in some cases. In some embodiments, the entire length of the stent graft 202 between the second balloon 220 and the catheter hub 240 is an uncovered portion 204. In some embodiments, only a proximal-most portion (as shown) of the stent graft 202 is an uncovered portion 204.

Still referring to FIG. 4, in some embodiments, provisions can be made to perfuse a branch vessel such as the contralateral iliac artery 16. For example, when the entire length of the stent graft 202 between the second balloon 220 and the catheter hub 240 is an uncovered portion 204, the contralateral iliac artery 16 will receive perfusion. That is the case because blood flowing through the lumen of the stent graft 202 will be allowed to exit the stent graft 202 in the uncovered area(s) proximal to the second balloon 220 and to then flow into the contralateral iliac artery 16. Alternatively, the stent graft 202 can include one or more open areas (not occluded by covering material; e.g., perforations, fenestrations, etc.) in the region proximal to the second balloon 220 near to where the contralateral iliac artery 16 branches off from the aorta 10. In that arrangement, blood flowing through the lumen of the stent graft 202 will be allowed to exit the stent graft 202 through the open areas proximal to the second balloon 220 and to then flow into the contralateral iliac artery 16.

Figure 6:
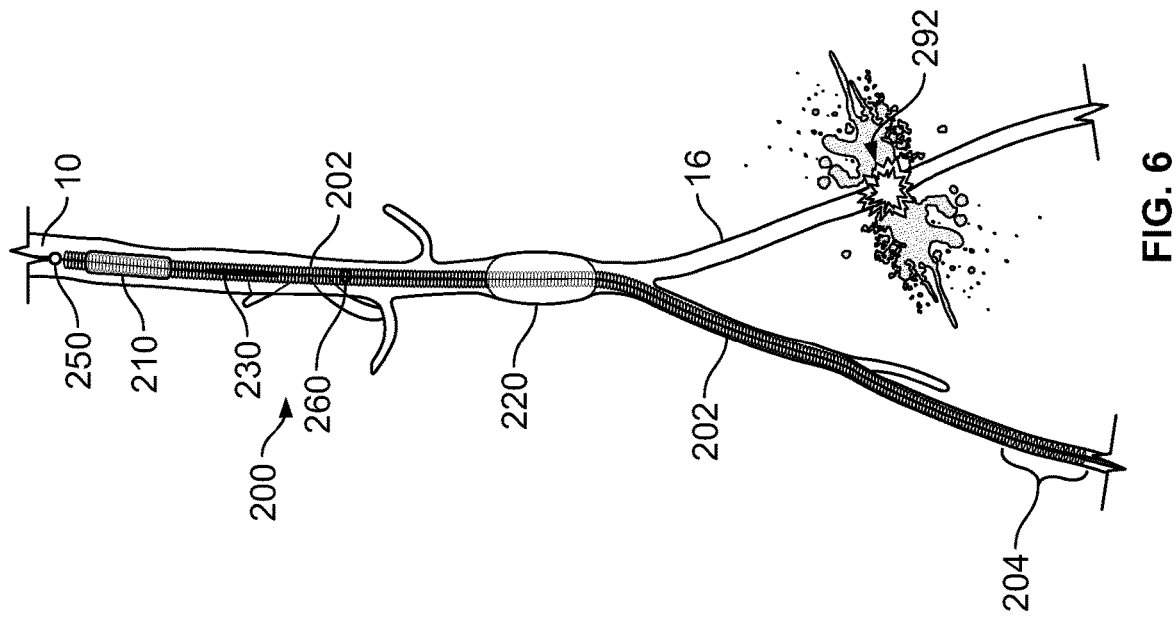
FIG. 6 is another illustration of a portion of a human vasculature, including a hemorrhage site, being treated using the endovascular device of FIG. 4.
Figure 5:
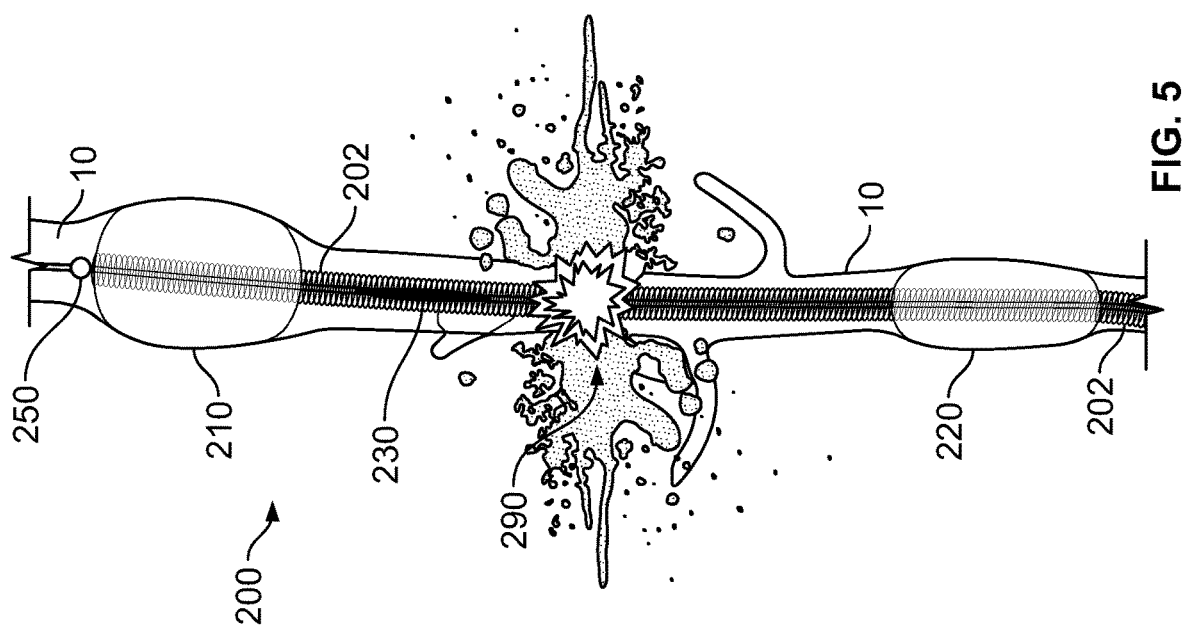
FIG. 5 is an illustration of a portion of a human vasculature, including a hemorrhage site, being treated using the endovascular device of FIG. 4.

Referring also to FIGS. 5 and 6, in some implementations, the endovascular stent graft device 200 is configured to serve as an endovascular-vascular shunt to aid in rapid cessation of various types of non-compressible hemorrhages associated with the aorta or other vessels. Alternative configurations of the endovascular stent graft device 200 can be implemented to provide occlusions of vessels dependent on the site of injury. In some embodiments, such alternative configurations can be automatically made by the control unit 280 in conjunction with the endovascular stent graft device 200.

For visceral injuries (as shown in FIG. 5), the first and second balloons 210 and 220 are inflated to prevent blood flow to the injury 290, while the third balloon 230 remains deflated, which allows blood perfusion of the lower extremities and pelvis by shunting blood through the stent graft 202.

In the event of a pelvic injury (as depicted by FIG. 6), the endovascular stent graft device 200 can be deployed and configured to allow blood flow to upstream branch vessels and the adjacent branching pelvic vessel while mitigating hemorrhage from the injury 292 in the branching leg vessel 16. In a first example, pertaining to the depicted embodiment that includes a fully covered stent graft 202 between the second balloon 220 and the uncovered portion 204, both the first balloon 210 and the third balloon 230 can be deflated (while the second balloon 220 is inflated). In result, blood will be allowed to flow between the exterior surface of the first balloon and the inner wall of the vessel 10. Such blood flow will thereby nourish branch vessels (such as the renal arteries, etc.). In addition, blood will flow within the lumen of the stent graft 202 to nourish the adjacent branching pelvic vessel. However, blood flow to the injury 292 in the branching leg vessel 16 will be substantially cut off. In a second example, pertaining to embodiments that have uncovered or open areas in the stent graft 202 proximally adjacent to the second balloon 220, the first balloon 210 can be deflated and the third balloon 230 can be inflated (while the second balloon 220 is inflated). By deflating the first balloon 210, blood flow will thereby be allowed to nourish branch vessels (such as the renal arteries, etc.) that are upstream of second balloon 220. By inflating third balloon 230, blood will be prevented from flowing through the lumen of the stent graft 202 and exiting through open or uncovered areas of the stent graft 202 to flow into the branching leg vessel 16. Hence, blood flow to the injury 292 will be substantially cut off.

In some embodiments, sensors 250 and 260 embedded in or coupled to the stent graft 202 can determine the location of the injury (e.g., injury 290, injury 292, and the like) by detecting hemodynamic changes within the patient's vasculature to determine and automatically (or semi-automatically) control the selective function of the separate balloons 210, 220, and 230.

Referring to FIGS. 12 and 13, again the distal end portion of endovascular stent graft device 200 is shown within the vessel 10. In the depicted configurations, both the first balloon 210 and the third balloon 230 are deflated. These figures illustrate that the construction of the stent member of stent graft 202 can differ at various locations along the stent graft 202. For example, in FIG. 12, the stent member is one or more braided wires, and the angle of the braid differs at various locations along the stent graft 202. In particular, the braid angle is more radial at the locations of the balloons 210 and 230, while the braid angle is more longitudinal at non-balloon locations. In the example of FIG. 13, portions of the stent member are made of expanded metallic material while other portions are made of braided metallic wire. In particular, the portion of the stent member underlying the first balloon 210 is braided wire, while the other portions of the stent member are expanded material. It should be understood that any and all combinations of stent constructions, and locations of such stent constructions, are envisioned within the scope of this disclosure.

Figure 14:
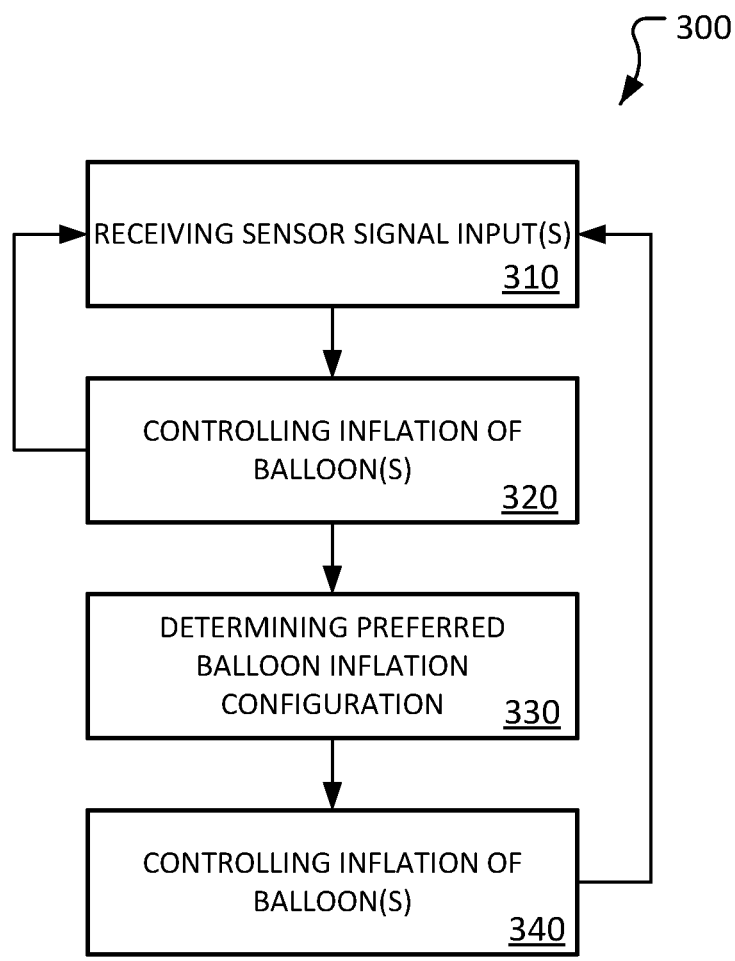
FIG. 14 is a flowchart of an example method of controlling the endovascular device of FIG. 4 using a computerized control unit.

FIG. 14 provides a flowchart of an example method 300 for controlling the endovascular device 200 of FIG. 4 by a computerized control unit (e.g., control unit 280). The method 300 is performed while the endovascular device 200 is within the vasculature of the patient and the computerized control unit is coupled with the endovascular device 200.

It should be understood that automating the control of the endovascular device 200 can be particularly advantageous in the emergency care setting. That is the case because emergency situations can be quite chaotic, and humans may have difficulties properly diagnosing and treating hemorrhage conditions is such situations. Hence, by automating or semi-automating the use of the endovascular device 200, better patient outcomes may be realized in some cases.

At step 310, the computerized control unit receives input signals from one or more sensors of the endovascular device. For example, at step 310 the computerized control unit can receive signals that are indicative of blood pressure and/or blood flow rates from one or more sensors such as the sensors 250 and/or 260 of the endovascular device 200. Such one or more sensors can additionally or alternatively be located at one or more other locations along the endovascular device 200. In addition, as described above, signals that are indicative of various other relevant parameters (blood gases (e.g., $O_2$, $CO_2$, etc.), temperature, pH, heart rate, etc.) can be received by the computerized control unit.

At step 320, the computerized control unit controls the inflation and deflation of the balloons of the endovascular device. For example, using the endovascular device 200 to illustrate this step, in some cases the computerized control unit may inflate first balloon 210, inflate third balloon 230, and deflate second balloon 220. After doing so, the method 300 can revert to step 310 and the computerized control unit can receive a second round of input signals from the one or more sensors 250 and 260 of the endovascular device 200. The control unit, knowing which balloons are inflated and deflated, can use the second round of input signals from the one or more sensors 250 and 260 in step 330 described below. After receiving the second round of input signals, the control unit may control the inflation of the balloons again (e.g., in another configuration) per step 320. Thereafter, the control unit can once again receive another round of input signals (per step 310) from the one or more sensors 250 and 260 of the endovascular device 200. The steps 320 and 310 can be repeated for multiple cycles. In some cases, for each time step 320 is performed, the particular configuration of balloon inflation/deflation can be different. By performing these repetitive steps, in some cases the control unit can obtain the data it needs to diagnose the location of a hemorrhage.

At step 330, the computerized control unit uses the data from the repetitive performance of steps 310 and 320 (as described above) to determine a preferred balloon inflation and/or deflation configuration. For example, using the endovascular device 200 to illustrate this step, the data from the repetitive performance of steps 310 and 320 may indicate that a hemorrhage may be located between the first and second balloons 210 and 220 (as exemplified in FIG. 5). Using such information, the computerized control unit may determine that the preferred balloon inflation and/or deflation configuration is to inflate first balloon 210, inflate second balloon 220, and deflate balloon 230. It should be understood that this is merely one non-limiting example of how the computerized control unit can perform step 330.

At step 340, after determining the preferred balloon inflation and/or deflation configuration in step 330, the control unit controls the inflation and/or deflation of the balloon(s) to implement the preferred balloon inflation and/or deflation configuration. For example, the control unit may inflate first balloon 210, inflate second balloon 220, and deflate balloon 230 (e.g., per FIG. 5). In another example, the control unit may deflate first balloon 210, inflate second balloon 220, and deflate third balloon 230 (e.g., per FIG. 6). It should be understood that multiple other variations of the preferred balloon inflation and/or deflation configuration that can be implemented in step 340 are also envisioned within the scope of this disclosure.

A number of embodiments of the invention have been described. Nevertheless, it will be understood that various modifications may be made without departing from the scope of the invention. Accordingly, other embodiments are within the scope of the following claims.

What is claimed is:

1. An endovascular device comprising:
   a stent graft comprising an expandable tubular metallic frame and a covering material disposed on at least a portion of the metallic frame, the stent graft defining a lumen that extends between a first end of the stent graft and a second end of the stent graft;
   a first balloon disposed on an outer periphery of the stent graft; and
   a second balloon disposed within the lumen, the second balloon having a fully inflated configuration that fully occludes the lumen and a partially inflated configuration that partially occludes the lumen for modulating blood flow through the stent graft.

2. The endovascular device of claim 1, wherein the first balloon fully surrounds the outer periphery of the stent graft.

3. The endovascular device of claim 1, further comprising:
   a first sensor coupled to the stent graft; and
   a second sensor coupled to the stent graft,
   wherein the first sensor and the second sensor are each configured to detect fluid pressure or blood flow rate.

4. The endovascular device of claim 3, wherein the first sensor is located distally of the second balloon and the second sensor is located proximally of the second balloon.

5. The endovascular device of claim 1, wherein at least a portion of the stent graft is diametrically tapered along a longitudinal length of the stent graft.

6. The endovascular device of claim 1, wherein at least a portion of the metallic frame is not covered by the covering material.

7. The endovascular device of claim 6, wherein an end portion of the metallic frame is not covered by the covering material.

8. The endovascular device of claim 1, wherein a middle portion of the stent graft includes one or more open areas that are not covered by the covering material, and wherein portions of the stent graft immediately adjacent on each side of the one or more open areas are covered by the covering material.

9. The endovascular device of claim 1, further comprising at least one sensor coupled to the stent graft and configured for detecting blood gases or pH.

10. The endovascular device of claim 1, further comprising:
    a third balloon disposed on the outer periphery of the stent graft and spaced apart from the first balloon.

11. The endovascular device of claim 10, wherein the second balloon is disposed within the lumen at a location along the stent graft between the first balloon and the third balloon.

12. A system for controlling catastrophic bleeding from vessels, the system comprising:
    an endovascular device comprising:
       a stent graft comprising an expandable tubular metallic frame and a covering material disposed on at least a portion of the metallic frame, the stent graft defining a lumen that extends between a first end of the stent graft and a second end of the stent graft;

a first balloon disposed on an outer periphery of the stent graft; and a second balloon disposed within the lumen, the second balloon having a fully inflated configuration that fully occludes the lumen and a partially inflated configuration that partially occludes the lumen for modulating blood flow through the stent graft; and a control unit coupleable to the endovascular device and configured for delivering inflation media to at least one of the first and second balloons.

13. The system of claim 12, further comprising a first sensor coupled to the stent graft, wherein the first sensor is configured to detect fluid pressure or blood flow rate.

14. The system of claim 13, further comprising a second sensor coupled to the stent graft, wherein the second sensor is configured to detect fluid pressure or blood flow rate.

15. The system of claim 14, wherein the first sensor is located distally of the second balloon and the second sensor is located proximally of the second balloon.

16. The system of claim 15, wherein the control unit is configured to receive signals indicative of fluid pressure or blood flow rate from each of the first sensor and the second sensor, and wherein the control unit is configured to control a delivery of inflation media to one or more of the first and second balloons based on one or more of the signals indicative of fluid pressure or blood flow rate.

17. A method for controlling catastrophic bleeding from vessels, the method comprising:

deploying an endovascular device in a blood vessel, the endovascular device comprising:

a stent graft comprising an expandable tubular metallic frame and a covering material disposed on at least a portion of the metallic frame, the stent graft defining a lumen that extends between a first end of the stent graft and a second end of the stent graft;

a first balloon disposed on an outer periphery of the stent graft; and a second balloon disposed within the lumen, the second balloon having a fully inflated configuration that fully occludes the lumen and a partially inflated configuration that partially occludes the lumen for modulating blood flow through the stent graft.

18. The method of claim 17, further comprising inflating the first balloon such that blood in the blood vessel flows in the lumen rather than flowing between the first balloon and a wall of the blood vessel.

19. The method of claim 18, further comprising coupling a control unit to the endovascular device, wherein the control unit is configured for delivering inflation media to at least one of the first and second balloons via one or more catheters coupled to the stent graft.

20. The method of claim 19, wherein the control unit performs the inflating of the first balloon in response to one or more blood pressure signals from one or more sensors coupled to the stent graft.

* * * * *